United States Patent

Haberl et al.

[11] Patent Number: 5,215,099
[45] Date of Patent: Jun. 1, 1993

[54] SYSTEM AND METHOD FOR PREDICTING CARDIAC ARRHYTHMIA UTILIZING FREQUENCY INFORMATITON DERIVED FROM MULTIPLE SEGMENTS OF THE LATE QRS AND THE ST PORTION

[76] Inventors: Ralph Haberl, Georgenstrasse 3A; Gerhard Steinbeck, Georgenstrasse 12, both of D-8033 Planegg, Fed. Rep. of Germany

[21] Appl. No.: 707,244

[22] Filed: May 23, 1991

Related U.S. Application Data

[63] Continuation of Ser. No. 629,094, Dec. 17, 1990, abandoned, which is a continuation of Ser. No. 374,470, Jun. 30, 1989, abandoned.

[51] Int. Cl.$^5$ ............................................. A61B 5/04
[52] U.S. Cl. ................................. 128/702; 364/413.06
[58] Field of Search .............. 128/695, 696, 702, 703, 128/704, 705, 706; 364/413.05, 413.06

[56] References Cited

U.S. PATENT DOCUMENTS

| | | | |
|---|---|---|---|
| 4,592,367 | 6/1986 | Imran | 128/706 |
| 4,679,144 | 7/1987 | Cox et al. | 128/702 |
| 4,680,708 | 7/1987 | Ambos et al. | 364/417 |
| 4,732,158 | 3/1988 | Sadeh | 128/702 |
| 4,742,458 | 5/1988 | Nathans et al. | 364/417 |
| 4,802,491 | 2/1989 | Cohen et al. | 128/702 |
| 4,947,857 | 8/1990 | Albert et al. | 128/696 |

OTHER PUBLICATIONS

Haberl R., "Frequency Analysis of the ECG With Maximum Entropy Method (MEM) versus Fast Fourier Transform (FFT) for Identification of Patients With Ventricular Trachycardia," *Circulation Supplement*, Part II, vol. 76, No. 4 (Oct. 1987), p. IV-182.

Primary Examiner—William E. Kamm
Assistant Examiner—George Manuel
Attorney, Agent, or Firm—Fitch, Even, Tabin & Flannery

[57] ABSTRACT

Several hundred digitized ECG waveforms are averaged together (discarding abnormal waveforms) to form an array of digitized values. Then multiple overlapping subsegments are extracted from this array, processed by a window function in a way that produces a D.C. free result, and transformed into the frequency domain. The logarithm of the square of the amplitude (down to a minimum noise threshold level) of these frequency domain values are then plotted in a three-dimensional plot that graphically illustrates whether or not the patient from whom the waveforms were taken is likely to be at risk of cardiac arrhythmia in the near future. Cross correlation of these functions against one far removed from the QRS complex enables a factor of normality to be computed.

33 Claims, 4 Drawing Sheets

SYSTEM AND METHOD FOR PREDICTING CARDIAC ARRHYTHMIA UTILIZING FREQUENCY INFORMATITON DERIVED FROM MULTIPLE SEGMENTS OF THE LATE QRS AND THE ST PORTION

This application is a continuation of application Ser. No. 629,094 filed Dec. 17, 1990 now abandoned, which is a continuation of Ser. No. 374,470, filed Jun. 30, 1989, now abandoned.

BACKGROUND OF THE INVENTION

The invention relates to electrocardiography, and more particularly to an improved electrocardiographic system and method for predicting potential ventricular tachycardia and other forms of cardiac arrhythmia.

Sudden death from acute cardiac arrhythmia, in particular ventricular tachycardia, is a major risk in the first few hours after a myocardial infarction. During the first days after a myocardial infarction the incidence of ventricular arrhythmia is approximately 90%. The percentage of arrhythmias decreases considerably after the first several days but still presents a substantial risk to the myocardial infarct patient. Statistically, without treatment, approximately 50% of all myocardial infarct patients will eventually die of ventricular tachycardia.

U.S. Pat. No. 4,458,692 for System and Method for Predicting Ventricular Tachycardia With a Gain Controlled High Pass Filter, which issued to Michael Simson, teaches how a series of successive ECG waveforms may be captured, converted into digital form, and averaged together (after the exclusion of abnormal or nontypical waveforms) to provide a relatively noise-free composite waveform. Simson filters this averaged waveform using reverse or bidirectional filtering with a high-pass filter having a corner frequency of 25 Hz. Simson then computes the root-mean-square (RMS) value of the voltage in the filtered tail segment of the QRS complex. In addition, Simson measures the width of the QRS complex after the filtering. Simson uses this RMS voltage measurement and this width measurement as indications of whether or not the patient is likely to be subject to ventricular tachycardia.

The Simson method just described is inapplicable to patients suffering from bundle branch block, and it cannot always distinguish between meaningful high frequency components at the trailing edge of the QRS complex, which may indicate a predisposition to ventricular tachycardia, and noise that originates from power line disturbances or muscles or the like.

More recently, in an effort to extract more useful diagnostic information from the ECG signal, researchers have utilized Fourier transformations to process ECG waveforms. See, for example, FIG. 2 in an article by Michael E. Cain, et al., entitled, "Quantification of Differences in Frequency Content of Signal-Averaged Electrocardiograms in Patients With Compared To Those Without Sustained Ventricular Tachycardia," Vol. 55, American Journal of Cardiology, 1500 (June 1, 1985). That figure shows a frequency domain representation of the X, Y, and Z lead signals from patients with and without ventricular tachycardia. Energy, expressed as voltage squared, is plotted against frequency. Cain et al. teach that "frequencies above 70 Hz did not contribute substantially to the terminal QRS and ST segments in any group." Frequencies between 50 Hz and 70 Hz were not analyzed by Cain et al. because of potential 60 Hz power line interference. The Cain 25 et al. analysis was limited to a single Fourier transformation of a lengthy segment that included both the 40 millisecond terminal portion of the QRS complex and also the entire ST part of an averaged ECG waveform preprocessed with a Blackman-Harris window function to minimize spectral leakage. Cain et al.'s rationale for performing Fourier analysis of such an extended length segment, treating it as a single unit, was to "enhance frequency resolution." Cain et al.'s analysis of the frequency domain data was limited to the frequency range of from 20 Hz to 50 Hz.

While these prior art approaches to the problem both recognize that the presence of high frequency components in the trailing portions of the QRS complex can identify patients likely to experience cardiac arrhythmia, these approaches do not adequately address the practical problem of providing the physician with clear and unambiguous information presented in a form that is simple to understand and utilize. These approaches also do not enable the physician to distinguish high frequency components indicative of cardiac arrhythmia from high frequency components attributable to muscle noise and the like.

SUMMARY OF THE INVENTION

In addition to recognizing that frequencies at and above 60 Hz are useful and meaningful, the present invention recognizes that a proper analysis of such high frequency components requires a determination of the background levels of such components and a comparison of these background levels to the level of similar components in the trailing portions of the QRS Complex and the ST part where their presence may be indicative of tachycardia. In addition, the present invention has as a primary object the presentation of the information to the physician in a way that is readily understandable and usable without the need for extensive training.

Briefly summarized, the present invention in its preferred form begins by amplifying (using a low-noise amplifier), filtering (with a low-pass filter having a cut-off frequency in the range of 300 Hz to 500 Hz), digitizing (at the rate of 1000 12-bit digital samples per second), and averaging together a large number (100 or so) of ECG waveforms, discarding nontypical waveforms. The averaged ECG waveform is then represented by an array containing about 200 16-bit data values in which the noise level is near or, preferably, below one microvolt. (The present invention does not require the averaged ECG waveform to be filtered using a reverse or bidirectional high pass filter of the type utilized by Simson).

Next, 20 to 60, preferably 25, segment data sets, each containing 80 16-bit data values, are extracted from this array and are analyzed individually for their frequency content. These segments (often referred to herein as subsegments to distinguish from larger portions or segments of the waveforms) are shifted in time relative to each other by 1 to 3 milliseconds, preferably 3 milliseconds. The first of these subsegments (the earliest in time) includes 20 milliseconds of the trailing portion of the QRS complex of the ECG waveform and 60 milliseconds that fall within the ST part (total size 80 milliseconds). The last of these subsegments (the latest in time) serves primarily as a reference for background noise and interference and begins 55 milliseconds (with 25 segments and shift 3 milliseconds) beyond the QRS complex.

The data within each of these subsegments are first multiplied point-by-point by a Hanning or Blackman-Harris window function to minimize the effects of subsegment edge discontinuities. If the resulting subsegment data contain a direct current component, then the original (un-multiplied) subsegment data are adjusted and are re-multiplied by the Hanning or Blackman-Harris window function, with the adjustment being chosen such that no direct current component appears within the subsegment data following the window function multiplication step.

Next, the time domain data within each subsegment is transformed into frequency domain data, preferably by means of a fast Fourier transform (FFT) algorithm. The resulting frequency domain data are plotted in a three-dimensional plot in which, for each subsegment, frequency is plotted against the logarithm (base 2.0) of the square of the values, with values falling below a minimum noise threshold level set to that minimum level to eliminate the noise from the plots and to make the data simpler to interpret. The third dimension of the plot represents time and illustrates the changes in the magnitude-versus-frequency plots from one subsegment to the next. Using a two-dimensional printer or display, a three-dimensional plot may be achieved by plotting curves for magnitude-versus-frequency for each individual subsegment in two dimensions, with the curves for the differing subsegments shifted a small increment from one plot to the next but otherwise substantially overlapping. As can be seen in the accompanying drawings, such three-dimensional plots reveal clearly the existence of the high-frequency components that are strong indicators of the likelihood of future cardiac arrhythmias. Of particular importance, because these three-dimensional plots reveal information about the distribution in time of high-frequency components both close to and within the QRS complex as well as far removed from the QRS complex, these plots enable a physician to recognize and to distinguish muscle noise and other high frequency interference components from components indicative of cardiac arrhythmia by the fact that noise components appear fairly uniformly in all of the subsegment frequency domain plots, whereas components indicative of arrhythmia appear predominantly in the subsegment plots that correspond to time segments close to and partially overlapping the QRS complex time interval. Accordingly, muscle noise and interference that might have caused a physician using the Simson technique to falsely conclude a patient was a likely candidate for future cardiac arrhythmias are readily identified for what they are by a physician utilizing the teachings of the present invention.

To further assist the physician in reaching a proper diagnosis, the present invention in its preferred form uses cross correlation techniques to compare and contrast the frequency distribution waveforms corresponding to subsegments positioned (in time) varying distances from the QRS complex. A factor of normality, scaled from zero to 100 percent, may be provided that can be understood even by physicians who do not know how to read and interpret the 3-dimensional plots which other physicians may prefer to study directly.

A more detailed description of the preferred embodiment of the invention, and further objects and advantages of the invention, are set forth in the drawings, in the detailed description which follows, and in the claims annexed to and forming a part of this specification. The invention itself is defined with particularity in the claims.

DETAILED DESCRIPTION OF THE PREFERRED EMBODIMENT

Figure 1:
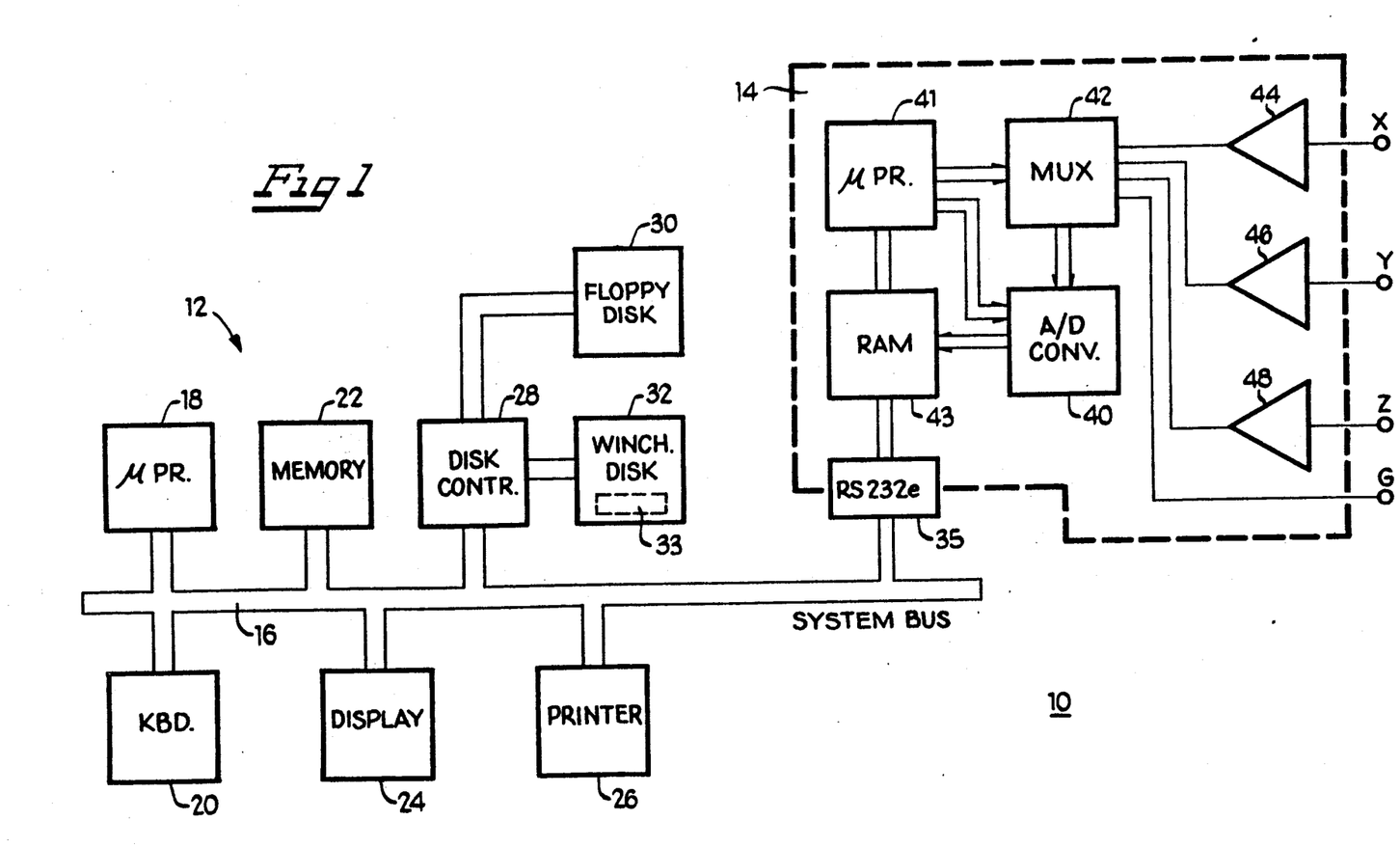
FIG. 1 is an overview block diagram of an apparatus 10, including a data acquisition unit 14 designed to collect ECG data from the human body and a computer 12 designed to process such data in accordance with the teachings of the present invention.

Referring to the drawings and especially to FIG. 1, an apparatus embodying the present invention is generally shown therein and is identified by the numeral 10. The apparatus 10 comprises a conventional IBM PC/AT compatible computer 12 having an electrocardiographic data acquisition unit 14 connected thereto. The computer 12 includes a system bus 16 for carrying data, address, control, and timing information between the various modules of the computer 12, all of which are well known to those skilled in the art. A microprocessor 18 is connected to the system bus 16 for communication therewith. A keyboard unit 20 is connected to the system bus 16 for communication therewith, as is a memory 22 comprising both read only memory (or ROM) and random access memory (or RAM), a video display card and display 24, and a printer 26. A disk controller 28 is connected for communication to the system bus 16, and a floppy disk 30 and a Winchester or rigid disk 32 are connected to the disk controller 28 for communication therewith. All of these aforementioned elements comprise the conventional microcomputer system 12.

Also connected to the system bus 16 through a detachable RS-232c data link 35 is a portable data acquisition unit 14 which, for example, may be an acquisition module model 1200EPX (Part No. 99-1200) which may be obtained from Arrhythmia Research Technology, Inc., Austin, Tex. This data acquisition unit 14 includes a microprocessor 41 having a RAM memory 43 that is battery powered to retain its contents for extended periods. The unit 14 also contains an analog-to-digital converter 40 that is connected to a multiplexer 42, and both are controlled by the microprocessor 41. The multiplexer 42 is connected to an X-lead bipolar electrocardiographic amplifier 44, a Y-lead bipolar electrocardiographic amplifier 46, and a Z-lead bipolar electrocardiographic amplifier 48 which are adapted to be connected via respective bipolar leads X, Y, and Z and a ground lead G to a patient for the sensing of electrocardiographic signals from the patient's body, as is well known to those skilled in ECG technology.

In practice, a nurse carries the unit 14 to the patients, records their ECGs, and then connects the unit 14 to the computer 12 by plugging the unit 14 into the computer's RS-232c data link 35 and commanding the two microprocessors 18 and 41 to transfer the digitized ECG data from the RAM 43 to the RAM portion of the memory 22 and ultimately to the Winchester disk 32 under software control.

Each of the amplifiers 44, 46, and 48 is a low-noise electrocardiographic amplifier that amplifies and passes signals from close to D.C. to an upper limit that falls within the range of about 300 to 500 Hz (at or below one-half the sampling rate). These amplifiers 44, 46, and 48 are also designed to electrically isolate the lines X, Y, Z, from all sources of power and from each other.

The multiplexer 42 and the analog-to-digital convertor 40 enable voltage levels at the output of all three amplifiers 44, 46, and 48 to be sampled 1,000 times each second, thereby producing 1,000 12-bit digital samples each second from the output of each of the three amplifiers 44, 46, and 48.

The digital samples thus collected represent successive ECG waveforms. These samples are initially stored in the RAM memory 43. In a manner similar to that which is fully described in U.S. Pat. No. 4,442,459 to Simson for Electrocardiographic Means and Method for Detecting Potential Ventricular Tachycardia, the samples for successive ECG waveforms may each be matched to a QRS template, and those samples corresponding to waveforms which do not match the template or which are otherwise abnormal are not retained. The remaining multiple digital samples representing a succession of input ECG waveforms can then be broken up into a plurality of arrays of data each containing the samples for one input ECG waveform. The data within each of these arrays are placed into phase with the data from the other arrays, and the amplitudes of data values representing waveform amplitude at corresponding points in time (relative to the QRS waveform) within the arrays are then averaged over many waveforms (for example, over 200 waveforms) to reduce the noise from muscle potentials and power line interference and the like to a minimum. This averaging process is preferably carried out with a resolution of at least 16 data bits. The resulting single array 33 of averaged data is ultimately transferred out of the RAM 43, conveyed across the RS-232c data link 35, and stored on the surface of the Winchester disk 32.

The array 33 of averaged data may contain only the average of just the X lead waveforms, or of just the Y lead waveforms, or of just the Z lead waveforms; alternatively, it may contain the sum of all of these separately-monitored X, Y, and Z waveforms. The array 33, which represents the time average of a series of ECG waveforms that were taken from a single patient, is then analyzed for late potentials indicative of ventricular tachycardia in accordance with the teachings of the invention.

Figure 6:
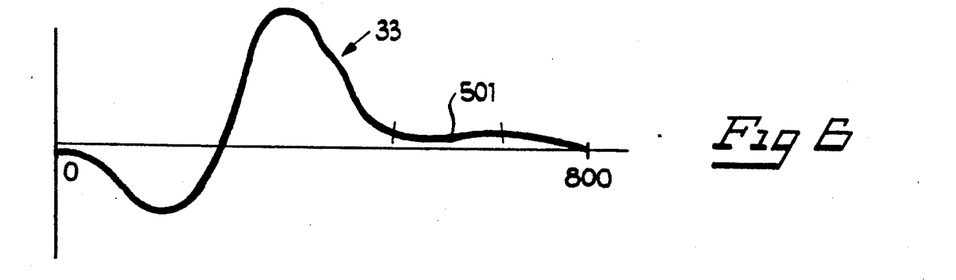
FIG. 6 is a plot of the data contained in an array of digitized, averaged ECG waveform data.

A hypothetical typical array 33 of averaged data is shown plotted in FIG. 6. The array 33 contains 800 16-bit samples, and the samples are spaced apart in time from each other by one microsecond.

Note that the hardware configuration shown in FIG. 1, in which the computer 12 is used in conjunction with the data acquisition unit 14, is only one of many possible configurations that may be utilized when implementing the present invention. For example, all of the above could have been carried out by the computer 12, rather than by the unit 14, and the unit 14 could have been a simple accessory to the computer 12. The array 33 could have been transferred from the unit 14 to the computer 12 on a floppy diskette or sent over a parallel data transmission channel, an infrared optical link, or a radio or magnetic coupling link. The computer 12 could have been omitted entirely, if the data acquisition unit 14 were sophisticated enough to carry out the remaining steps and had a suitable printer or display or both.

Figure 2:
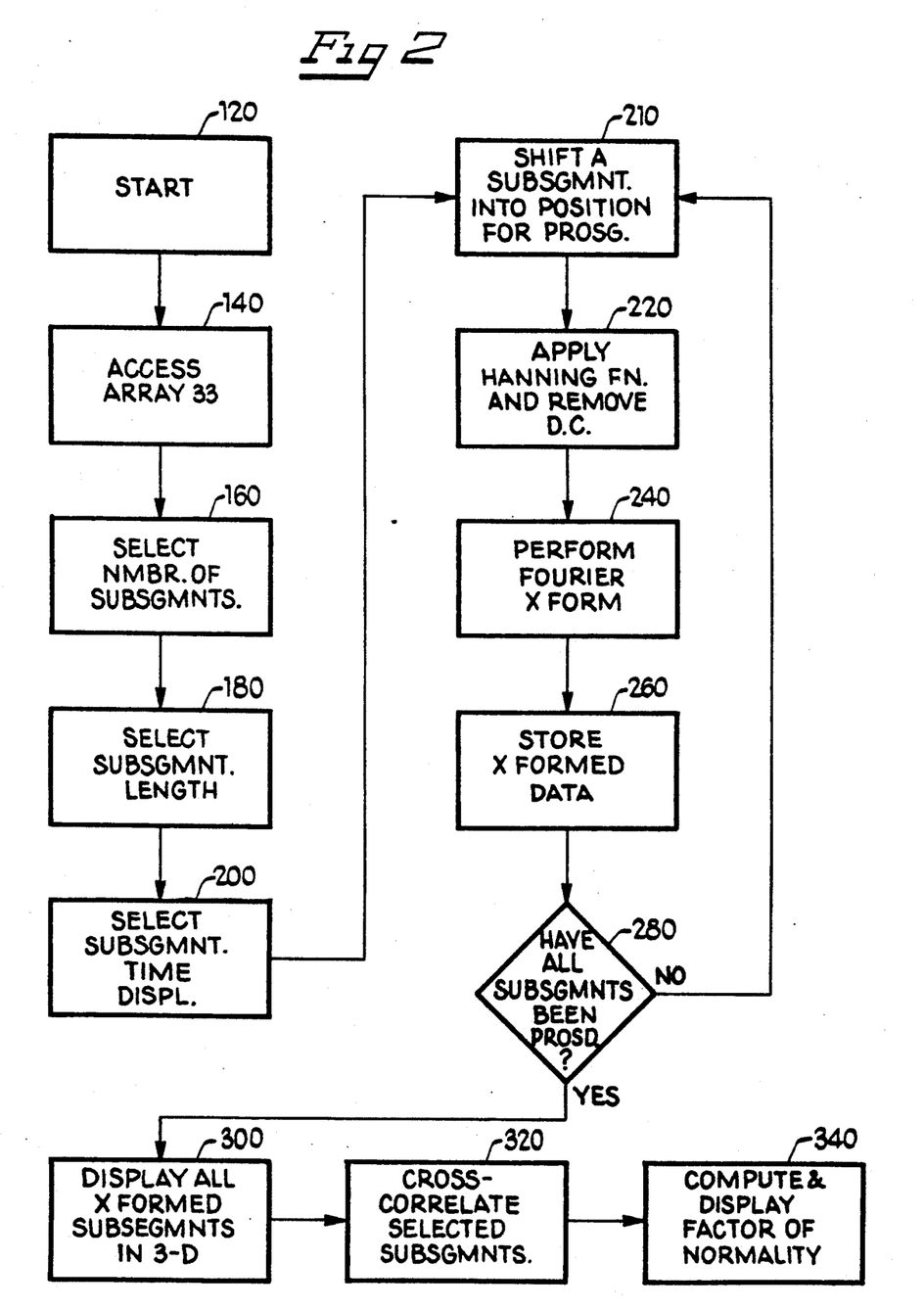
FIG. 2 is a flow chart of some of the operations that are performed by the computer 12 shown in FIG. 1.

As may best be seen in FIG. 2, the microprocessor 18 processes the array 33 of averaged data, starting at a starting step 120, and ultimately displays the processed information on the printer 26 and/or the display 24 at step 300 and computes and displays a factor of normality at a step 340. Data processing begins with a step 140, where the microprocessor 18 retrieves the array 33 of averaged data from its storage place on the Winchester disk 42 and places the array 33 into the RAM portion of the memory 22 in preparation for further processing.

A plurality of options may then be presented on the display 24 to the the user of the system 10. At step 160, the user is asked to select the number of subsegments of the array 33 that are to be evaluated. Optimally, 25 subsegments are selected for evaluation. Step 180 then prompts the user to specify the length of the subsegments of the array 33, and step 200 prompts the user to specify their displacement from each other in time. As was previously indicated, the present inventors have found the optimum subsegment length to be 80 milliseconds and the optimal time displacement of adjacent subsegments to be about 3 milliseconds. The user may also be asked what type of window filtering is to be applied to each segment —none, Blackman-Harris, or Hanning—with the Hanning window function being the optimal choice. Another possible user-selectable variable is the starting time of the first (or earliest in time) subsegment. In the preferred embodiment of the invention, the first data sample in the first subsegment is chosen such that about one-fourth of the data samples constituting the first subsegment fall within the QRS complex, and the remaining data samples fall within the ST part of the ECG waveform.

Next, the microprocessor 18 enters into a repetitive loop operation which extends from step 210 through step 280 in FIG. 2. One pass through this loop is executed for each of the 25 subsegments of the array 33 that needs to be processed, and during each pass only that portion of the array 33 constituting a single subsection is processed.

FIG. 6 is a graphical representation of the data within the array 33 of averaged data plotted amplitude against time. While this plot, and the remaining plots in FIGS. 7 through 10, are shown as continuous plots, it will be understood that the data plotted are actually an array of 800 (FIG. 6) or 512 (FIGS. 7 through 10) 16-bit integers. The plots shown in FIGS. 6 through 10 are not plots of actual data but simply rough approximations to what these plots would look like if they were presented in this fashion, in contrast to the plots of FIGS. 3A, 4A and 5A which were generated by a computer-controlled plotter. In FIG. 6, each data value represents an ECG sample spaced in time one millisecond from the adjacent samples.

A typical 80 millisecond subsection of the array 33, one of the 25 subsections that are to be analyzed individually, is identified in FIG. 6 by the reference numeral 501. The subsection 501 contains 80 16-bit digital samples or data values, and 25 such subsets shifted three milliseconds in time with respect to each other are utilized in the preferred embodiment of the invention. However, only one illustrative subsegment is shown in FIG. 6 for clarity. The digital samples may be conveniently stored as floating point numbers having sufficient resolution to preserve their accuracy through the computations that follow.

Figure 7:
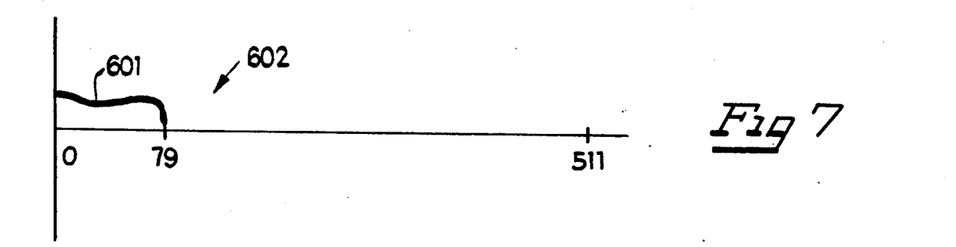
FIG. 7 is a plot of the data contained in a subsegment 501 of the array 33 shown in FIG. 6 shifted to the right end of a 512 data element array 602 to facilitate fast Fourier transformation of the data.

At step 210, the data values forming the subsection 501 are shifted into position for fast Fourier transform processing. With reference to FIG. 7, a 512 element data array 602 is established. The data values forming the subsection 501 in FIG. 6 are positioned in FIG. 7 in a left-shifted subsection 601 of the array 602 as array data values zero through 79 of the 512-element array 602. The remaining data values in the array 602 are set to zero. In this manner, the number of data values is an even power of two—a requirement of the fast Fourier transform algorithm that will later be applied to the data, as is well known. Note that other types of time-domain to frequency-domain transformation algorithms suitable for use in implementing the present invention may not require the length of the subsegment arrays to be extended in this manner.

Figure 8:
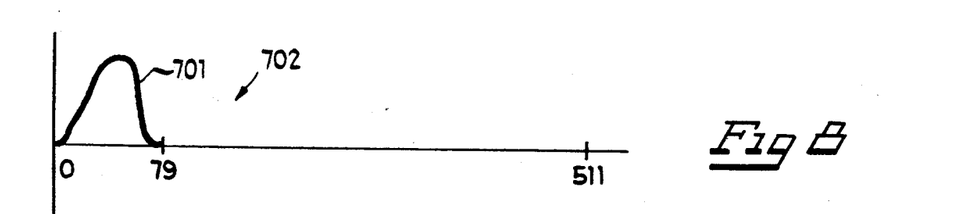
FIG. 8 is a plot of a Hanning window function that is applied to the data shown in FIG. 7.
Figure 9:
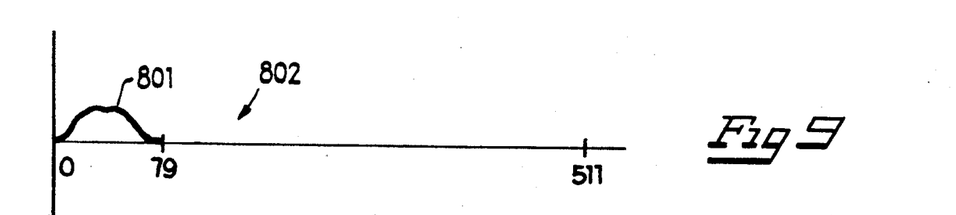
FIG. 9 is a plot of the same data shown in FIG. 6 after multiplication by the Hanning window function shown in FIG. 8, illustrating the presence of an undesirable D.C. component.

At step 220, each data value in the subsection 601 of the array 602 is multiplied by a corresponding data value in the Hanning window function which is shown at 701 in FIG. 8, giving rise to a new subsection 801 of a new array 802 that is shown in FIG. 9. Next, the new subsection 801 is analyzed to see how large a D.C. component it contains. Then the data values in the subsection 601 in FIG. 7 are individually adjusted upwards or downwards, each by the same amount, as is needed so that after multiplication by the Hanning window function data values 701, a second new subsection 901 of an array 902 (FIG. 10) is generated which has no D.C. component. It is important to the proper functioning of the invention that this D.C. component elimination process be carefully done.

Figure 10:
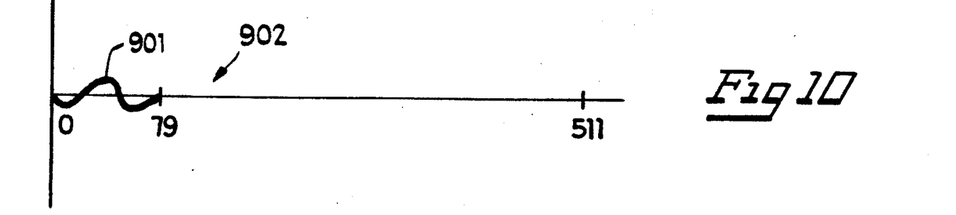
FIG. 10 is a plot of the data shown in FIG. 6, adjusted to correct the D.C. component problem illustrated in FIG. 9, after multiplication by the Hanning window function shown in FIG. 8.

As an example of the above steps, the following routine, written in Microsoft Basic, is utilized on an IBM compatible computer in the preferred embodiment of the invention to perform the D.C. component elimination and Hanning function filtering steps (program comments are indented for clarity):

```
           Program steps to preprocess the data values for
           one of the 25 subsegments -- repeated 25 times.
           Program definitions:
DELTA = 80
           DELTA equals 80, the number of elements in each
           of the 25 subsegments of the ECG waveform.
DIM LEAD(800)
           LEAD( ) is the array 33 of averaged data
           (FIG. 6). It contains one floating point data
           value per millisecond, 800 samples total.
BW = QRSOFF − 20
           BW is the position of the start of a subset 501
           (FIG. 6) within the array 33 of averaged data
           (FIG. 6). Initially, BW is set to address,
           within the array LEAD( ), the data value
           positioned 20 milliseconds to the left of the
           data value at the right end of the QRS complex.
           After each subsegment is processed by the
           following program and is then fast Fourier
           transformed, the value of BW is incremented by 3,
           and then the next subsegment is processed and
           transformed in the same manner. This process is
           repeated until all 25 subsegments have been
           processed and transformed.
           QRSOFF, the position of the data value at the
           terminal end of the QRS complex, is computed (by
           code not shown) to be the point where the rate of
           change of the ECG at the trailing edge of the QRS
           complex decreases to below 5 millivolts per
           second. This definition allows a clear
           definition of the end of the QRS complex even in
           patients with bundle branch block.
API = 3.141592654#
           API is pi, or 3.141592654
DIM SEGM(512)
           SEGM( ) is, at different times, the array 602
           (FIG. 7), then the array 802 (FIG. 9), and
           finally the array 902 (FIG. 10). Ultimately,
           SEGM( ) contains the subsegment data values (plus
           zero fill to the right) in a form suitable for
           the fast Fourier transformation step 240 (FIG.
           2).
DIM WIND(512)
           WIND( ) is loaded with the Hanning window
           function 701 (FIG. 8).
DIM TEMP(512)
           TEMP( ) is also the array 602 (FIG. 7) at all
           times (a duplicate copy of the array data). It
           is used in the D.C. offset adjustment step 220.
           Shift the data values that comprise a selected
           subsegment 501 (FIG. 6) of the array of averaged
           data 33 which is named LEAD( ) into a subsegment
           601 (FIG. 7) at the beginning of a 512-integer
           array 602, and fill in the remainder of the array
           602 with zero fill. Two copies of the array 602
           are created (SEGM( ) and TEMP( )). Load zero
           values into the terminal portion of the array
           WIND( ).
FOR QQ = 0 TO DELTA
   SEGM(QQ) = LEAD(QQ + BW)
   TEMP(QQ) = SEGM(QQ)
NEXT QQ
FOR QQ = DELTA TO 512
   SEGM(QQ) = 0
   TEMP(QQ) = 0
   WIND(QQ) = 0
NEXT QQ
           Compute Hanning window function data values 701
           (FIG. 8) and store them in the array 702 (FIG. 2)
           which is named WIND( ) and which already contains
           zero values in its terminal portion.
FOR QQ = 0 TO DELTA
   WIND(QQ) = WIND(QQ)*.5*(1 − COS(2*(QQ −
   1)*API/DELTA))
NEXT QQ
```

-continued

```
    Multiply the Hanning window function data values
    701 (FIG. 8) by the corresponding data values in
    the subsegment 601 (FIG. 7) in the array SEGM( ),
    giving the subsegment values 801 (FIG. 9) which
    remain in the array SEGM( ), ignoring D.C. bias
    for the moment.
TOTS = 0
TOTW = 0
FOR QQ = 0 TO DELTA
    SEGM(QQ) = SEGM(QQ) * WIND(QQ)
    TOTS = TOTS + SEGM(QQ)
    TOTW = TOTW + WIND(QQ)
NEXT QQ
    At this point, SEGM( ) is the array 801 shown in
    FIG. 9 uncorrected for D.C. bias. TOTS is the
    total D.C. offset of the data values in the
    segment 801 (or SEGM( )), and TOTW is the total
    D.C. offset of the window function data values
    701 in the array WIND( ).
    Compute the D.C. bias correction that must be
    applied to the subsegment 601 data values:
DCOFF = TOTS / TOTW
    DCOFF is now the amount of D.C. bias correction
    that must be applied to each data value in the
    subsegment 601 shown in FIG. 7, and still stored
    in the array TEMP( ), prior to multiplication by
    the Hanning function data values 701 stored in
    the array WIND( ).
    Now multiply the Hanning function data values 701
    in the array WIND( ) by the D.C.-bias-corrected
    subsegment 601 data values stored in the array
    TEMP( ) to give the subsegment 901 data values
    901 (FIG. 10) in the array SEGM( ).
FOR QQ = 0 TO DELTA
    SEGM(QQ) = (SEGM(QQ) - DCOFF) * WIND(QQ)
NEXT QQ
```

Step 240 in FIG. 2 next performs a fast Fourier transformation upon the resulting 512-element array 902 (FIG. 10). Step 260 then stores the transformed data.

A test is then made at step 280 to determine whether all 25 subsegments have been converted to frequency domain representations. If not, then program control is passed back to the steps 210, 220, 240, and 260 which proceed to process the next subsegment in a like manner, and again the test defined by 280 is performed to determine whether all the subsegments 501 segments have been converted.

The fast Fourier transform is a well-known mathematical transformation that needs not be described here. Alternatively, a standard Fourier transformation may be used or other equivalent types of transformations (La Place, Wignee-Ville, autoregressive models) may be utilized to transform the data segments from their time domain form into a frequency domain form that reveals the spectral distribution of energy within each subsegment.

Figures 3A, 3B:
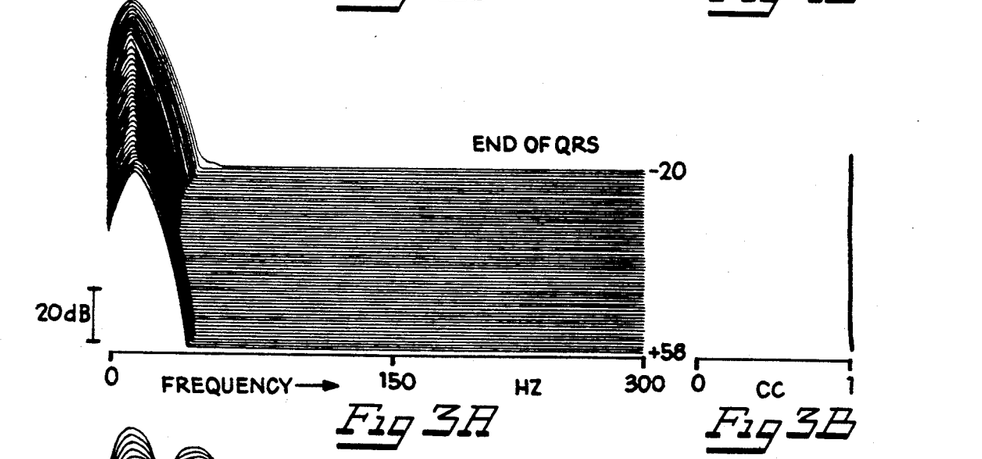
FIG. 3A is a mapping with Fourier transform of a plurality of overlapping, time-shifted, 80-millisecond subsegments of the terminal portion of the QRS segment and of the ST segment of an averaged ECG waveform in which frequency is plotted against the logarithm of the square of amplitude, taking 60 subsegments, with 1 millisecond time shift, starting 20 milliseconds inside the QRS complex; these plots, by their uniformity, indicate that the patient is unlikely to experience ventricular tachycardia.
FIG. 3B is a plot of the correlation coefficient (CC) corresponding to FIG. 3A.
Figures 4A, 4B:
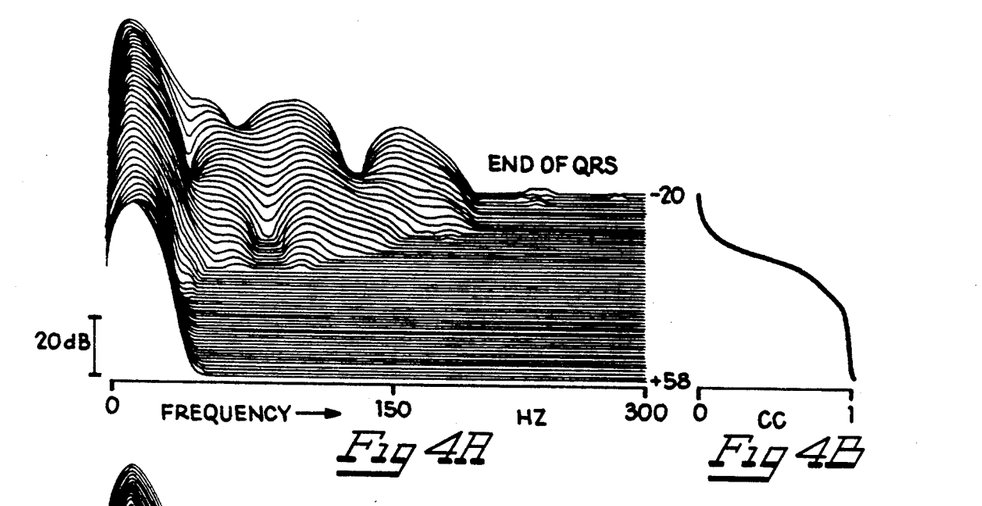
FIG. 4A is a mapping with Fourier transform of a plurality of overlapping, time-shifted subsegments similar to those shown in FIG. 3 but in which the relatively low uniformity from subsegment to subsegment indicates the presence of high frequency late potentials in the terminal portion of the QRS complex which indicate that the patient is likely to experience ventricular tachycardia.
FIG. 4B is a plot of the correlation coefficient (CC) corresponding to FIG. 4A.
Figures 5A, 5B:
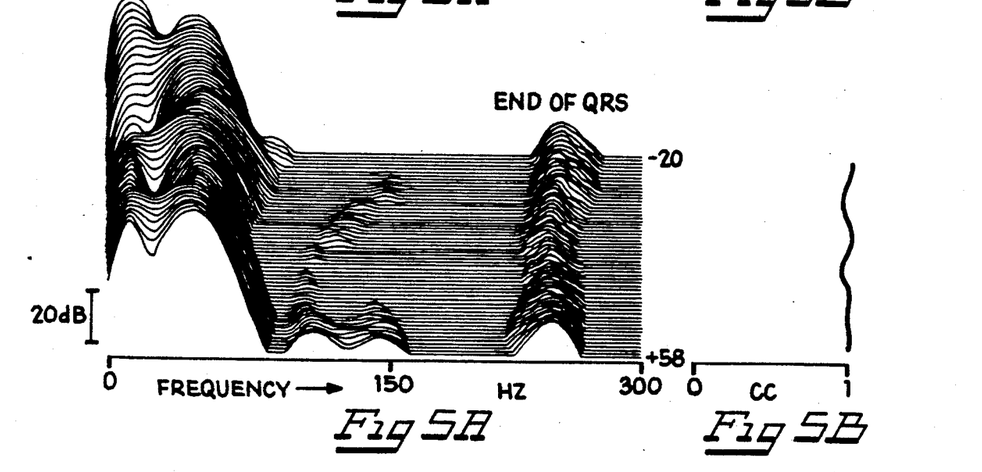
FIG. 5A is a mapping with Fourier transform of a plurality of overlapping time-shifted subsegments similar to those shown in FIGS. 3A and 4A, wherein the signal being analyzed is noisy.
FIG. 5B is a plot of the correlation coefficient (CC) corresponding to FIG. 5A.

Once all 25 of the subsegments have been converted, they are displayed and/or printed simultaneously in the form of a three-dimensional plot, as is illustrated in FIG. 3A for a normal patient and in FIG. 4A for a patient who is likely to suffer from cardiac arrhythmia. For each curve, the horizontal axis represents frequency ranging from zero up to 300 Hz. The vertical axis represents the logarithm (base 2.0) of the amplitude squared down to some predetermined minimum threshold noise level, at which point each curve becomes a straight line, as shown. This noise threshold, which may be user user adjustable or which may be factory preset to avoid user confusion, is adjusted to give a curve such as those shown in FIGS. 3A and 4A, with low level background noise eliminated entirely from the plots as shown.

The individual curves of separately transformed subsegment data are shifted downwards with respect to each other, as is shown in FIGS. 3A and 4A, so that as one moves downwards from one curve to the next, one moves forward in time by 1 millisecond. Note that as one moves downwards, one is moving away (in time) from the QRS complex, and the curves normally become flatter and eventually flatten out to straight lines, as in the two examples shown. However, had there been higher levels of background noise or interference present, the curves would not have flattened out. See FIG. 5A. Instead, all of the curves would have contained similar undulations reflecting the frequency content of the noise or interference spread evenly over the entire time interval represented by the three dimensional plot, reflecting the fact that through the averaging process any such interference, which is assumedly not synchronized with the heart beat, appears at differing times during different heartbeats and therefore, in an averaged waveform, appears to some degree in all of the plotted curves.

This fact has led the present inventors to develop a cross-correlation routine which, by measuring the similarity of the waveforms at the extreme ends of the time interval of interest in the plots of FIGS. 3A and 4A. The spectra are compared to a reference spectrum with cross correlation. The result is 25 correlation coefficients. A coefficient of 1 means that two spectra are identical, a coefficient of 0 means that there is no similarity between the two spectra. Typically, at step 320, the mean coefficient of the first five subsegments in the set of 25 is compared to the mean coefficient of the last five subsegments, and a "factor of normality" is calculated as described below. If the factor of normality is less than or equal to 30%, late potentials are not likely to be present. The cross-correlation result is displayed (FIGS. 3B, 4B and 5B) on the display 24 and/or on the printer 26 in step 340 (FIG. 2).

It may be appreciated that one important feature of the invention lies in the fact that an assumption is made that the noise characteristics of the signal are relatively constant. Thus, since the late potentials may be concentrated in only a portion of the subsegments taken from the segment being examined, the correlation coefficient is relatively low, as late potentials are only present in some segments and not in others. Noise results in a high correlation across segments, since the noise spectrum is relatively constant throughout all the subsegments of interest. Thus, it may be appreciated that the inventors have provided a quick and easy test for indicating the likelihood of ventricular tachycardia occurring in which likelihood may be determined either by visual examination of the graphical material of FIG. 3a and FIG. 4a or by means of the correlation coefficient (FIG. 3B or FIG. 4B) or the factor of normality computed in accordance with step 340.

The specific method whereby the factor of normality is computed is the following: The frequency spectrum of the subsegment displaced farthest away from the QRS complex is taken as a reference spectrum, and it is cross correlated, over the frequency range of 40 Hz to 150 Hz, against the frequency spectrum of the remaining segments. The results are 25 correlation coefficients which fall within the range zero to 1, where zero indicates no similarity and 1 indicates that two spectra are identical. Then the mean of the cross correlation coefficients of subsegments nearest QRS complex are divided by the mean of the correlation coefficients for the five segments furthest from the QRS complex (=quotient1). Then the whole spectral content within the range 40 to 150 Hz is determined for the same sets of five subsegments each, the difference of which is called "diff1". "Diff1" is a high positive value, if the high frequency components at the end of QRS complex are more prominent than far outside the QRS complex. "Quotient 1" and "diff1" are combined into a "factor of normality" which ranges between zero and 100 percent.

While there have been illustrated and described particular embodiments of the present invention, it will be appreciated that numerous changes and modifications will occur to those skilled in the art which fall within the true spirit and scope of the present invention.

What is claimed is:

1. A system for providing an indication for determining the likelihood of a patient's experiencing cardiac arrhythmia from analysis of an electrocardiographic signal having a QRS Complex obtained from the patient, comprising:
    means for selecting a portion of an electrocardiographic signal of one heartbeat;
    means for detecting the trailing edge of the QRS Complex of said signal and for selecting a first segment of said portion, said first segment being in the vicinity of the trailing edge of the QRS Complex of said signal and having a time duration greater than 40 milliseconds, means for centering said first segment where cardiac arrhythmia signals are likely to be found;
    means for selecting a second segment of said portion, said second segment being away from the trailing edge of the QRS Complex of said signal and having a time duration greater than 40 milliseconds, and means for centering said second segment where cardiac arrhythmia signals are not likely to be found and where background signals predominate, and means for starting the time duration of said second segment and the time duration of said first segment at least 20 milliseconds apart;
    means for deriving a first frequency domain representation of said first segment;
    means for deriving a second frequency domain representation of said second segment; and
    means for comparing said first frequency domain representation and said second frequency domain representation and from said comparison providing an indication for determining the likelihood of said patient's experiencing a cardiac arrhythmia.

2. A system in accordance with claim 1 wherein said electrocardiographic segments are represented by time domain data values and wherein each of said means for deriving comprises means for transforming time domain data values into frequency domain data values.

3. A system in accordance with claim 2 wherein said means for comparing and providing comprises cross correlation means for cross correlating said first and second frequency domain representations.

4. A system in accordance with claim 3 which includes additional means for selecting additional segments of said portion, said additional segments time shifted with respect to each other and with respect to said first and second segments;
    which further includes additional means for deriving additional frequency domain representations of said additional segments,
    in which said cross correlation means correlates at least one of said frequency domain representations against the other representations, and
    in which said means for comparing and indicating further includes means for separately computing the average of the results of cross correlation with respect to plural segments near the QRS Complex of said signal and the average of the results of cross correlation with respect to plural segments not near the QRS Complex of said signal, means for computing the ratio of said averages, and means for outputting said ratio as an indication of said likelihood of cardiac arrhythmia.

5. A method for providing an indication for determining the likelihood of a patient's experiencing cardiac arrhythmia from analysis of an electrocardiographic signal having a QRS Complex obtained from the patient, comprising the steps of:
    selecting a portion of an electrocardiographic signal of one heartbeat;
    detecting the trailing edge of the QRS Complex of said signal and selecting a first segment of said portion, said first segment being in the vicinity of the trailing edge of the QRS Complex of said signal and having a time duration greater than 40 milliseconds, centering said first segment where cardiac arrhythmia signals are likely to be found;
    selecting a second segment of said portion, said second segment being away from the trailing edge of the QRS Complex of said signal and having a time duration greater than 40 milliseconds, centering said second segment where cardiac arrhythmia signals are not likely to be found and where background signals predominate, and starting the time duration of said second segment and the time duration of said first segment at least 20 milliseconds apart;
    deriving a first frequency domain representation of said first segment;
    deriving a second frequency domain representation of said second segment; and
    comparing said first frequency domain representation and said second frequency domain representation and from said comparison providing an indication for determining the likelihood of said patient's experiencing a cardiac arrhythmia.

6. A method in accordance with claim 5 wherein plural subsegments are selected in each said selecting step and wherein plural frequency functions are derived in each deriving step.

7. A method in accordance with claim 5 wherein the comparison of said first and second frequency functions is carried out through cross correlation of the functions.

8. A system for providing an indication for determining the likelihood of a patient's experiencing cardiac arrhythmia from an analysis of an electrocardiographic signal having a QRS Complex obtained from the patient, comprising:
    means for selecting a portion of an electrocardiographic signal of one heartbeat;
    means for detecting the trailing edge of the QRS Complex of said signal and for selecting a plurality of time-shifted near and far subsegments, said near subsegments being in the vicinity of the trailing edge of the QRS Complex, means for centering said near subsegments where cardiac arrhythmia signals are likely to be fond, and said far subsegments being away from the QRS Complex, means for centering said far subsegments where cardiac arrhythmia signals are not likely to be found and where background signals predominate, and means for starting the time duration of said far subsegments and the time duration of said near subsegments at least 20 milliseconds apart, said subsegments having a time duration greater than 40 milliseconds;

means for deriving a frequency domain representation of each of said subsegments; and means for outputting a three-dimensional plot of said frequency domain representation as an indication for determining the likelihood of said patient's experiencing a cardiac arrhythmia.

9. A method in accordance with claim 8 wherein the means for deriving comprises means for transforming time domain data values into frequency domain data values.

10. A method in accordance with claim 9 wherein the means for outputting plots one curve of frequency versus amplitude for each frequency function, with said curves plotted at physically shifted but substantially overlapping positions to give a three dimensional perspective representing the relative time displacements of the corresponding subsegments.

11. A system for providing indication permitting determination of the likelihood of a patient's experiencing cardiac arrhythmia from analysis of an electrocardiographic signal having a QRS Complex obtained from the patient, comprising:

means for selecting a portion of an electrocardiographic signal within the range of one heartbeat to be analyzed extending from just before the end of the QRS Complex to a point away from the QRS Complex where background signals predominate;

means for selecting a number of time-shifted segments of said selected portion approximately 80 milliseconds in length and substantially overlapping each other in time;

means for subjecting each of said time-shifted segments to a window function, yielding windowed time-shifted segments;

means for adjusting the D.C. signal content of each of said time-shifted segments to cause said windowed time-shifted segments to contain no D.C. component;

means for deriving a frequency domain representation comparable to a Fourier transform from each of said segments; and means for outputting a three-dimensional plot of said frequency domain representation as an indication permitting determination of the likelihood of said patient's experiencing a cardiac arrhythmia.

12. A method in accordance with claim 11 wherein said means for outputting includes means for plotting the square of each data value in the frequency domain representation logarithmically for all function values above a noise threshold level.

13. A system for providing indication permitting determination of the likelihood of a patient's experiencing cardiac arrhythmia from analysis of an electrocardiographic signal having a QRS Complex portion obtained from the patient, comprising the steps of:

selecting a portion of an electrocardiographic signal within the range of one heartbeat to be analyzed that extends from near the end of the QRS Complex to a location away from the QRS Complex that primarily contains background high frequency components;

selecting a number of time-shifted segments of said selected portion approximately 80 milliseconds in length and substantially overlapping each other in time;

subjecting each of said time-shifted segments to a window function, yielding windowed time-shifted segments;

adjusting the D.C. signal content of each of said time-shifted segments to cause said windowed time-shifted segments to contain no D.C. component;

deriving a frequency domain representation from each of the segments; and plotting the resulting frequency domain representations in a three-dimensional plot of the logarithm of the square of the representations down to a minimum noise threshold value below which the plot is not permitted to go;

whereby said plot provides indication permitting determination of the likelihood of said patient's experiencing cardiac arrhythmia.

14. A system for analyzing an electrocardiographic signal, comprising:

means for selecting a portion of an electrocardiographic signal to be analyzed within the range of one heartbeat;

means for selecting a number of time-shifted segments of said selected portion substantially overlapping each other in time;

means for subjecting each of said time-shifted segments to a window function, yielding windowed time-shifted segments;

means for adjusting the D.C. signal content of each of said time-shifted segments to cause said windowed time-shifted segments to contain no D.C. component;

means for deriving a frequency domain representation comparable to a Fourier transform from each of said segments; and means for outputting a three-dimensional plot of said frequency domain representation.

15. A method in accordance with claim 14 wherein said means for outputting includes means for establishing a minimum noise threshold value below which the plot is not permitted to go.

16. A method in accordance with claim 14 or claim 15 wherein said plot is a logarithmic plot of signal energy.

17. A method for analyzing an electrocardiographic signal, comprising the steps of:

selecting a portion of an electrocardiographic signal within the range of one heartbeat to be analyzed;

selecting a number of time-shifted, overlapping segments of said selected portion;

subjecting each of said time-shifted segments to a window function, yielding windowed time-shifted segments;

adjusting the D.C. signal content of each of said time-shifted segments to cause said windowed time-shifted segments to contain no D.C. component;

deriving a frequency domain representation from each of said segments; and plotting the resulting frequency domain representations in a three-dimensional plot of the representations.

18. A method in accordance with claim 17 wherein the three-dimensional plot plots the representations down to a minimum noise threshold bellow which the plot is not permitted to go.

19. A method in accordance with claim 17 or claim 18 in which the plot is a logarithmic plot of signal energy.

20. A system for analyzing an electrocardiographic signal, comprising:

means for averaging together a number of individual heartbeat components of said signal to give a relatively noise-free averaged signal within the range of one heartbeat;

means for selecting a number of time-shifted segments of at least a selected portion of said relatively noise-free averaged signal, said segments substantially overlapping each other in time;

means for subjecting each of said time-shifted segments to a window function, yielding windowed time-shifted segments;

means for adjusting the D.C. signal content of each of said time-shifted segments to cause said windowed time-shifted segments to contain no D.C. component;

means for deriving a frequency domain representation comparable to a Fourier transform from each of said windowed time-shifted segments, producing frequency domain representations of said windowed time-shifted segments; and means for outputting a three-dimensional plot of said frequency domain representations.

21. A method in accordance with claim 20 wherein the plot is a logarithmic plot of signal energy.

22. A method in accordance with claim 20 wherein said means for outputting includes means for establishing a minimum noise threshold value below which the plot is not permitted to go.

23. A method in accordance with claim 22 wherein the plot is a logarithmic plot of signal energy.

24. A method for analyzing an electrocardiographic signal, comprising the steps of:

averaging together a number of individual heartbeat components of said signal to give a relatively noise-free averaged signal within the range of one heartbeat;

selecting a number of time-shifted segments of at least a selected portion of said relatively noise-free averaged signal, said segments substantially overlapping each other in time;

subjecting each of said time-shifted segments to a window function, yielding windowed time-shifted segments;

adjusting the D.C. signal content of each of said time-shifted segments to cause said windowed time-shifted segments to contain no D.C. component;

deriving a frequency domain representations from each of the windowed time-shifted segments, producing frequency domain representations of said windowed time-shifted segments; and plotting the resulting frequency domain representations in a three-dimensional plot.

25. A method in accordance with claim 24 in which the plot is a plot of the logarithm of signal energy.

26. A method in accordance with claim 24 in which the plotting step plots the resulting frequency domain representations down to a minimum noise threshold value below which the plot is not permitted to go.

27. A method in accordance with claim 26 in which the plot is a plot of the logarithm of signal power. energy.

28. A system for providing an indication for determining the likelihood of a patient's experiencing cardiac arrhythmia from analysis of an electrocardiographic signal having a QRS Complex obtained from the patient, comprising:

means for selecting a portion of an electrocardiographic signal of one heartbeat;

means for detecting the trailing edge of the QRS Complex of said signal and for selecting a first plurality of near segments of said portion, said near segments being in the vicinity of the trailing edge of the QRS Complex of said signal, means for centering said first plurality where cardiac arrhythmia signals are likely to be found;

means for selecting a second plurality of far segments of said portion, said far segments being away from the trailing edge of the QRS Complex of said signal, and means for centering said second plurality where cardiac arrhythmia signals are not likely to be found and where background signals predominate, and means for starting the time duration of said far segments and the time duration of said near segments at least 20 milliseconds apart;

means for deriving near frequency domain representations of said near segments;

means for deriving far frequency domain representations of said far segments; and means for comparing said near frequency domain representations and said far frequency domain representations and from said comparison providing an indication for determining the likelihood of said patient's experiencing a cardiac arrhythmia.

29. A method in accordance with claim 28 wherein said electrocardiograph segments are represented by time domain data values and wherein each of said means for deriving comprises means for transforming time domain data values into frequency domain data values.

30. A method in accordance with claim 29 wherein said means for comparing and providing comprises cross correlation means for cross correlating said near and far frequency domain representations.

31. A method in accordance with claim 30 in which said means for comparing and indicating further includes means for separately computing the average of the results of cross correlation with respect to said near segments and the average of the results of cross correlation with respect to said far segments, means for computing the ratio of said averages, and means for outputting said ratio as an indication of said likelihood of cardiac arrhythmia.

32. A method for providing an indication for determining the likelihood of a patient's experiencing cardiac arrhythmia from analysis of an electrocardiographic signal having a QRS Complex obtained from a patient, comprising the steps of:

selecting a portion of an electrocardiographic signal of one heartbeat;

detecting the trailing edge of the QRS Complex of said signal and selecting a first plurality of near segments of said portion, said near segments being in the vicinity of the trailing edge of the QRS Complex of said signal, centering said first plurality where cardiac arrhythmia signals are likely to be found;

selecting a second plurality of far segments of said portion, said far segments being away from the trailing edge of the QRS Complex of said signal, centering said second plurality segments where cardiac arrhythmia signals are not likely to be found and where background signals predominate, and starting the time duration of said far segments and the time duration of said near segments at least 20 milliseconds apart;

deriving near frequency domain representations of said near segments;

deriving far frequency domain representations of said far segments; and comparing said near frequency domain representations and said far frequency domain representations and from said comparison providing an indication for determining the likelihood of said patient's experiencing cardiac arrhythmia.

33. A method in accordance with claim 32 wherein the comparison of said near and far frequency functions is carried out through cross correlation of the functions.

* * * * *

UNITED STATES PATENT AND TRADEMARK OFFICE
CERTIFICATE OF CORRECTION

PATENT NO. : 5,215,099
DATED : June 1, 1993
INVENTOR(S) : Haberl et al.

It is certified that error appears in the above-indentified patent and that said Letters Patent is hereby corrected as shown below:

Title Page:

Item [75], under "Inventors", change "Georgenstrasse 12" to --Georgenstrasse 12A--.

Item [54], in the title, change "INFORMATITON" to --INFORMATION--.

At column 1, line 4, change "INFORMATITON" to --INFORMATION--.

At column 2, lines 33-34, "Complex" should be --complex--.

At column 6, line 51, delete "the" (second occurrence).

At column 9, line 64, delete "user" (second occurrence).

At column 10, line 4, change "downwards" to --downward--.

At column 10, line 6, change "downwards" to --downward--.

At column 10, line 23, change "which, by measuring" to --which measures--.

At column 10, line 53, change "3a" to -- 3A --.

UNITED STATES PATENT AND TRADEMARK OFFICE
CERTIFICATE OF CORRECTION

PATENT NO. : 5,215,099
DATED : June 1, 1993
INVENTOR(S) : Haberl et al.

It is certified that error appears in the above-indentified patent and that said Letters Patent is hereby corrected as shown below:

At column 10, line 54, change "4a" to --4A--.

At column 11, line 18, in claim 1, change "patient's" to --patient--.

At column 11, line 51, in claim 1, change "patient's" to --patient--.

At column 12, line 15, in claim 5, change "patient's" to --patient--.

At column 12, line 45, in claim 5, change "patient's" to --patient--.

At column 12, line 55, in claim 8, change "patient's" to --patient--. 3).

At column 13, line 13, in claim 8, change "patient's" to --patient--.

At column 13, line 15, claim 9, change "method" to --system--.

At column 13, line 19, claim 10, change "method" to --system--.

At column 13, line 27, in claim 11, change "patient's" to --patient--.

UNITED STATES PATENT AND TRADEMARK OFFICE
CERTIFICATE OF CORRECTION

Page 3 of 4

PATENT NO. : 5,215,099
DATED : June 1, 1993
INVENTOR(S) : Haberl et al.

It is certified that error appears in the above-indentified patent and that said Letters Patent is hereby corrected as shown below:

At column 13, line 54, in claim 11, change "patient's" to --patient--.

At column 13, line 61, in claim 13, change "patient's" to --patient--.

At column 14, line 21, in claim 13, change "patient's" to --patient--.

At column 14, line 44, claim 14, change "method" to --system--.

At column 14, line 48, claim 16, change "method" to --system--.

At column 15, line 29, claim 21, change "method" to --system--.

At column 15, line 32, claim 22, change "method" to --system--.

At column 15, line 36, claim 23, change "method" to --system--.

At column 16, line 2, in claim 28, change "patient's" to --patient--.

UNITED STATES PATENT AND TRADEMARK OFFICE
CERTIFICATE OF CORRECTION

PATENT NO. : 5,215,099
DATED : June 1, 1993
INVENTOR(S) : Haberl et al.

It is certified that error appears in the above-indentified patent and that said Letters Patent is hereby corrected as shown below:

At column 16, line 32, in claim 28, change "patient's" to --patient--.

At column 16, line 33, claim 29, change "method" to --system--.

At column 16, line 38, claim 30, change "method" to --system--.

At column 16, line 42, claim 31, change "method" to --system--.

At column 16, line 52, in claim 32, change "patient's" to --patient--.

At column 18, line 4, claim 32, change "patient's" to --patient--.

Signed and Sealed this

First Day of November, 1994

Attest:

BRUCE LEHMAN

*Attesting Officer*   *Commissioner of Patents and Trademarks*